United States Patent [19]

Van der Knaap

[11] Patent Number: Plant 6,742

[45] Date of Patent: Apr. 18, 1989

[54] CHRYSANTHEMUM PLANT NAMED GUILDERLAND

[75] Inventor: Jacques C. M. Van der Knaap, De Lier, Netherlands

[73] Assignee: Fides Beheer B.V., De Lier, Netherlands

[21] Appl. No.: 124,546

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum named Guilderland having flat capitulum form and single anemone capitulum type, lavender pink ray florets, and its yellow tinged with pink disc florets.

1 Drawing Sheet

1

The present invention comprises a new and distinct cultivar of *Chrysanthemum morifolium,* hereinafter referred to by the cultivar name Guilderland.

Guilderland is a product of a planned breeding program which had the objective of creating new chrysanthemum cultibars with single anemone capitulum type, pink ray floret color, nine (9) weeks response, and the ability to produce commercially acceptable quality in year around cut mum programs. Such traits in combination were not present or needed improvement in previously available commercial cultivars.

Guilderland was originated from a hybridization made by applicant in a controlled breeding program in De Lier, Holland in 1980. The female parent was Maximo, and the male parent of Guilderland was Show-off.

Guilderland was discovered and selected as one flowering plant within the progeny of the stated parentage by applicant in April 1980 in a controlled environment in De Lier, Holland.

The first act of asexual reproduction of Guilderland was accomplished when vegetative cuttings were taken from the initial selection in June 1980 in a controlled environment in De Lier, Holland by a technician working under formulations established and supervised by applicant. Horticultural examination of selected units initiated in November 1980 has demonstrated that the combination of characteristics as herein disclosed for Guilderland are firmly fixed and are retained through successive generations of asexual reproduction.

Guilderland has not been observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Guilderland, which in combination distinguish this Chrysanthemum as a new and distinct cultivar:

1. Generally flat capitulum form.
2. Single (anemone) capitulum type.
3. Lavender pink ray florets.
4. Diameter across the face of the capitulum is 65–75 mm.
5. Pink green cushion (immature) to pink yellow (mature) disc florets.

Of the many commercial cultivars known to the present inventor, the most similar in comparison to Guilderland is the maternal parent Maximo. In comparison to

2

Maximo, Guilderland has better vigor and lavender pink ray florets, as opposed to the white ray florets of Maximo. The capitulum form and capitulum type are similar to those same characteristics of Maximo.

The accompanying photographic drawing shows in front view typical inflorescence and foliage characteristics of Guilderland, with colors being as nearly true as possible with illustrations of this type.

In the following description, color references are made to The Royal Horticultural Society Colour Chart. The color values were determined between 11:00 a.m. and 12:00 noon in September 1980 under natural daylight at De Lier, Holland.

Classification:

*Botanical.*—*Chrysanthemum morifolium,* Ramat., cv. Guilderland.

*Commercial.*—Cut anemone spray.

INFLORESCENCE

A. Capitulum:
- *Form.*—Flat when flowers open.
- *Type.*—Single anemone.
- *Diameter across face.*—65–75 mm.

B. Corolla of ray florets:
- *Color (general tonality from a distance of three meters).*—Lavender pink.
- *Color (upper surface).*—75C.
- *Color (lower surface).*—75D.

C. Corolla of disc florets:
- *Color (mature).*—Pink yellow, approximately 20B.
- *Color (immature).*—Pink green.

D. Reproductive organs:
- *Androecium.*—Present only in disc florets; few.
- *Gynoecium.*—Present in both disc and ray florets; numerous.

PLANT

A. General appearance:
- *Height.*—80 cm.

B. Foliage:
- *Color (upper surface).*—137A.
- *Color (under surface).*—147B.
- *Shape.*—Heavily indented and serrated.

I claim:

1. A new and distinct cultivar of Chrysanthemum plant named Guilderland, as illustrated and described, and parts thereof.

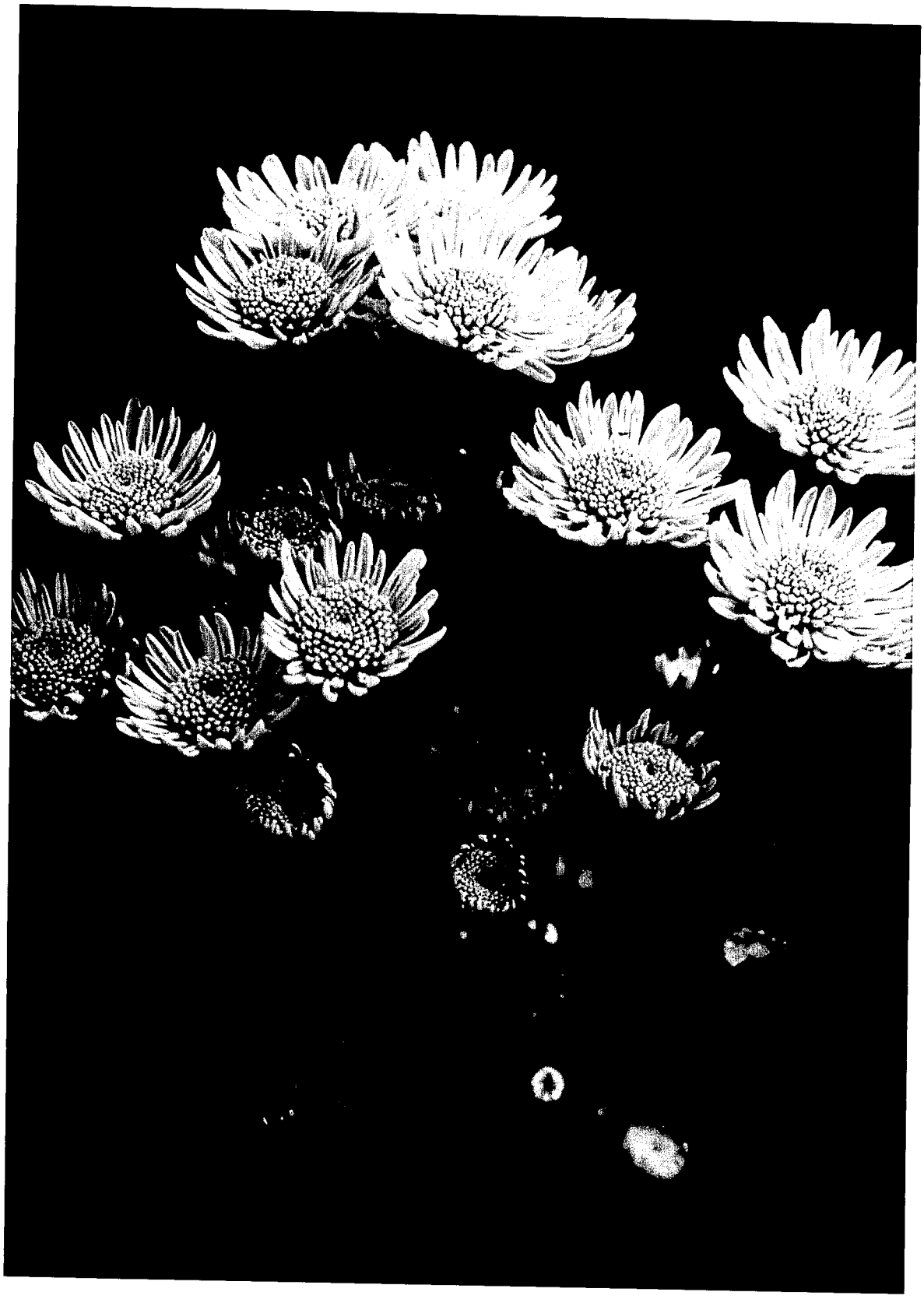

* * * * *